United States Patent [19]

Cohen

[11] 4,237,894
[45] Dec. 9, 1980

[54] MALE CATHETER

[76] Inventor: Milton J. Cohen, Potomac, Md.

[21] Appl. No.: 46,679

[22] Filed: Jun. 8, 1979

[51] Int. Cl.³ .............................................. A61M 25/00
[52] U.S. Cl. .............................................. 128/349 R
[58] Field of Search .................. 128/349 R, DIG. 26, 128/349 B, 349 BV, 350, 351

[56] References Cited

U.S. PATENT DOCUMENTS

| 1,207,479 | 12/1916 | Bisgaard | 128/349 R |
|---|---|---|---|
| 1,242,314 | 10/1917 | Bean | 128/349 R |
| 2,159,947 | 5/1939 | Gansol | 128/DIG. 26 |
| 2,820,457 | 1/1958 | Phillips | 128/DIG. 26 |
| 3,312,215 | 4/1967 | Silber | 128/349 X |
| 3,807,408 | 4/1974 | Summers | 128/349 R |
| 3,815,608 | 6/1974 | Spinosa et al. | 128/349 R |
| 4,089,337 | 5/1978 | Kronner | 128/349 B |
| 4,155,364 | 5/1979 | Boxer | 128/349 B |

FOREIGN PATENT DOCUMENTS 998906  10/1976  Canada .................. 128/349 B

Primary Examiner—Lawrence W. Trapp
Attorney, Agent, or Firm—McDougall, Hersh & Scott

[57] ABSTRACT

A catheter for use in male patients is disclosed. A catheter is inserted into the urethra and secured in position by the expansion of a flexible portion of the catheter to engage the fossa navicularus. In a first embodiment the expansion is controlled by a threaded element which is removably engaged in the catheter. In a second embodiment the flexible portion of the catheter is collapsible during insertion and expands to the secured position.

8 Claims, 4 Drawing Figures

MALE CATHETER

BACKGROUND OF THE INVENTION

This invention relates to catheters which are used to drain urine from the bladders of male patients.

Conventional catheters have one end inserted into a patient's urethral canal and positioned in the bladder while the remaining end is received in a urine receptacle. The catheter is then secured in position to prevent it from being expelled. The conventional or Foley catheter is secured in position by means of a diaphragm associated with the end of the catheter and which is inserted into the bladder and inflated. When the catheter is to be inserted or removed the membrane is in a deflated state. When the end of the catheter has been positioned within the bladder a syringe filled with sterilized water is used to force water into the inflatable membrane. The inflated membrane retains the end of the catheter in the bladder.

The Foley catheter is not without shortcomings. It is expensive to produce the bi-tubular catheter having the inflatable diaphragm. The securing of the catheter requires the use of a syringe which has been prefilled with sterile water. Another defect of this catheter is that it must sometimes remain in the patient for several days at a time and can irritate the bladder.

A dangerous disadvantage of this type of catheter is that misuse can cause serious injury to the patient. It is not uncommon for elderly or delirious patients to attempt and sometimes succeed in removing the catheter without deflating the membrane. This results in serious trauma to the patient's urethra.

It is accordingly an object of the present invention to provide an improved catheter which is low in cost, safe and easy to use and which can be secured in place without the need for an inflatable diaphragm.

It is a further object of the invention to provide a catheter which will not cause excessive trauma to the urinary track if it is improperly removed.

Other objects and advantages of the present invention will become apparent from the specifications which follow.

SUMMARY OF THE INVENTION

The foregoing objects of the invention are achieved by providing a catheter having a means to engage the fossa navicularus of the urethra to prevent it from being dislodged from the urinary canal.

DETAILED DESCRIPTION OF THE INVENTION

Figure 1:
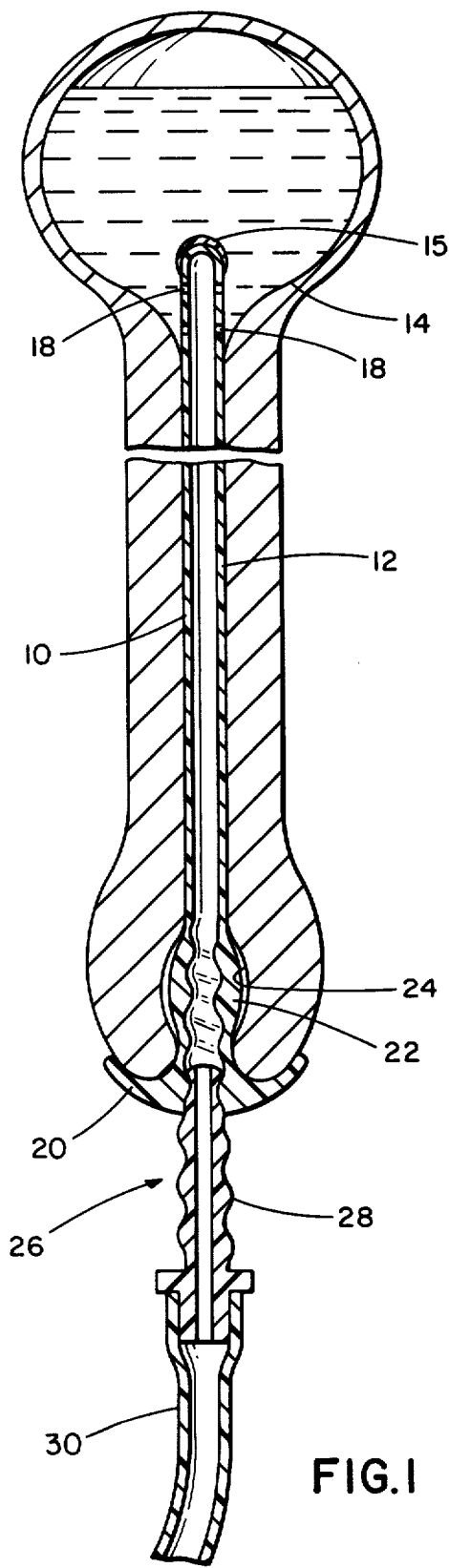
FIG. 1 is a cross-sectional view of the male urinary canal showing the preferred embodiment of the invention before it is locked into position against the fossa navicularus.

Referring to FIG. 1, the preferred embodiment of the invention is shown. The catheter is comprised of several sections including a hollow urethral tube 10 dimensioned to allow it to be passed upon the male urethra 12 and into the bladder 14. The inserted end 15 of this tube is occluded and formed into a generally hemispherical end. A plurality of holes 18 are provided adjacent to the end 15 of the tube. The other end of the urethral tube 10 is provided with a guard member 20 which is disposed over the head of the penis. A flexible threaded tube section 22 connects the guard to the tube 10 for a purpose to be described.

The invention utilizes a natural anatomical deviation or enlargement which occurs in the urethra within the glans of the penis. That deviation, illustrated at 24, is medically known as the fossa navicularus. When the urethral tube is inserted the flexible threaded portion thereof is located at the fossa navicularus. After insertion this portion is expanded to engage the fossa navicularus and secure the catheter in place.

To expand the threaded section 22 a threaded catheter lock 26 is provided. Lock 26 is hollow and relatively inflexible. It tapers from one end to the other and has external threads 28 provided thereon to engage the interior threads of the tube section 22.

Figure 2:
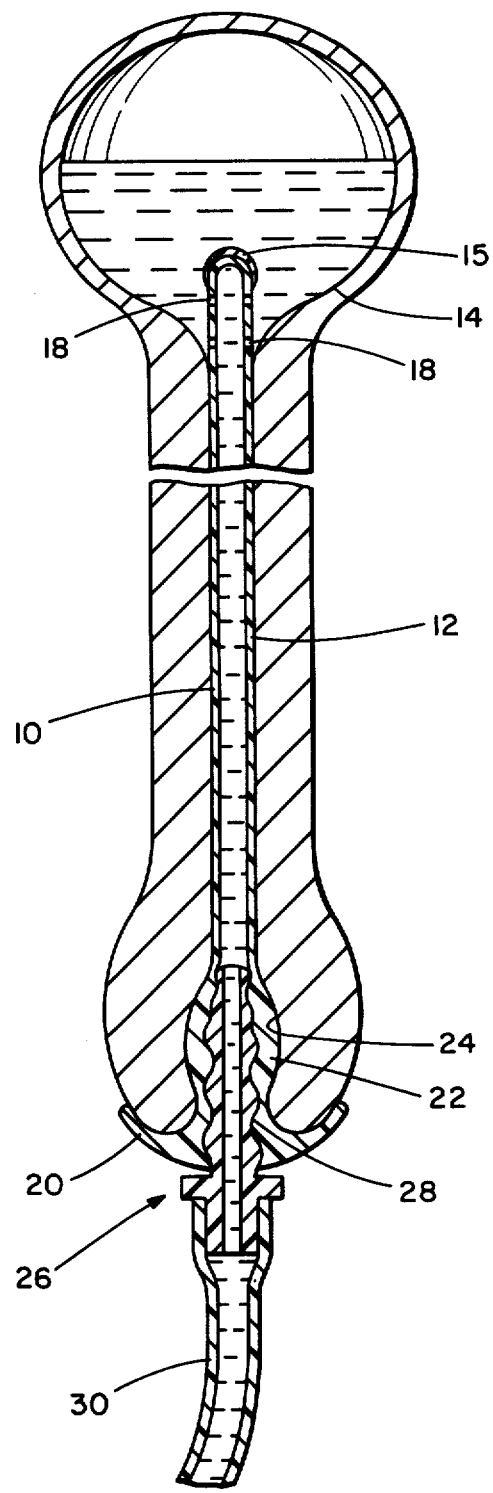
FIG. 2 is a cross-sectional view of the first embodiment of the invention secured into position.

To secure the catheter in position the lock 26 is threaded into the threaded portion 22 of the tube gradually expanding the latter until it engages the fossa. The external end of the lock is then connected by a tube 30 to a urine receptacle to complete the catheter assembly. The secured catheter is illustrated in FIG. 2.

When a patient is to be fitted with the catheter the following procedure is employed. The occluded end of the catheter is inserted into the urethral canal and is urged up towards the bladder. Since the threaded portion 22 is flexible it will be in a collapsed state and can also be inserted into the urethral canal until the guard member 22 is disposed against the end of the penis. Once the urethral tube is fully inserted the catheter lock is threaded into the tube causing the tube to expand to a shape which is complementary to the fossa.

Removal of the catheter is accomplished by reversing the indicated sequence. The tube 30 is removed, the lock is unthreaded and finally the tube 10 is withdrawn.

Figure 3:
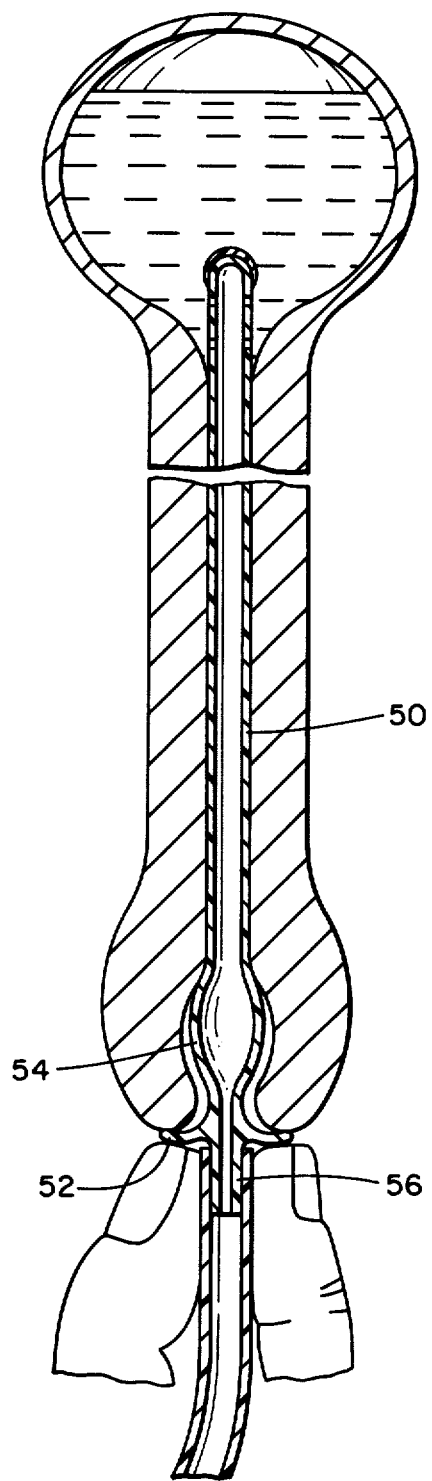
FIG. 3 is a cross-sectional view of the urinary canal and an alternate embodiment of the invention prior to securing the catheter.
Figure 4:
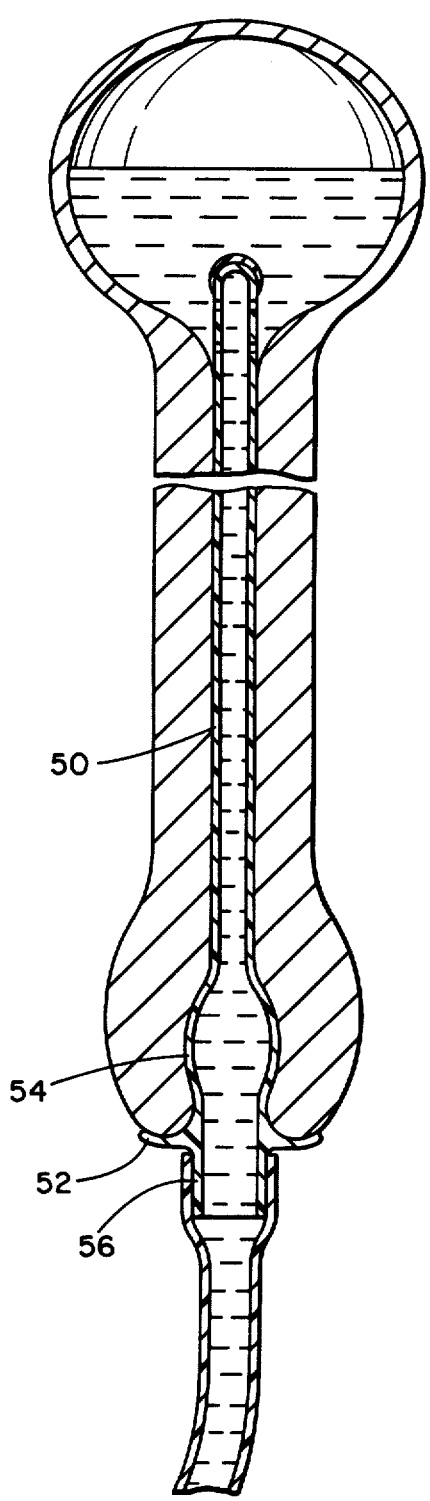
FIG. 4 is a view similar to FIG. 3 in the secured position.

FIGS. 3 and 4 illustrate an alternate embodiment of the invention. In this embodiment the catheter tube 50 has a guard member 52 attached at one end thereof by a flexible section 54. The guard member has a hollow cylindrical projecting portion 56 extending outwardly therefrom.

The urethral tube 50 is partially inserted into the urethra and the flexible section 54 is positioned close to the tip of the penis. The person fitting the catheter then pinches the projection portion 56 thereby to collapse the portion 54 to allow it to be inserted into the urethral canal. After the guard is correctly positioned the projection 56 is released and the flexible section 54 will expand to a shape complementary to the fossa.

The catheters herein described may be constructed of any resilient material which is not an irritant to the urinary canal, such as plastic or rubber. The length of the urethral canal will vary from patient to patient and is generally related to overall body size. Hence, hospitals which use the invention will have a variety of different size catheters.

While I have shown and described embodiments of this invention in some detail, it will be understood that this description and illustrations are offered merely by way of example, and that the invention is to be limited in scope only by the appended claims.

I claim:

1. A catheter for male species comprising
a hollow urethra tube adapted to be inserted into the male urethra through the glans penis to communicate the the male urethra through the glans penis to communicate the bladder with an external urine receptacle, one end of said tube being inserted and provided with a plurality of openings to permit urine to flow into the tube, the other end of said tube having a guard member secured thereto adapted to engage and seat against the head of the penis, said guard being secured to said tube by a flexible portion of said tube which can be manually expanded and reduced in diameter, and means for controlling expansion of said flexible portion, said tube being inserted with said flexible section in a reduced condition and subsequently expanded after the tube is in position, the expanding of said flexible section being effective to cause said section to engage the fossa navicularus to secure the catheter in position.

2. A male catheter comprising:
(a) a hollow urethra tube adapted to be inserted into the male urethra through the glans penis to communicate the bladder with external means for collecting urine,
(b) means for securing said tube in position by engaging the wall of the urethra at the fossa navicularus, said means including a flexible portion of said tube capable of expanding to conform to the shape of the fossa navicularus and
(c) means for controlling expansion of said flexible portion.

3. A catheter according to claim 1 or claim 2 wherein said flexible portion of said tube has internal threads formed therein and said means for controlling expansion is a locking member having complimentary external threads, expansion being accomplished by threading said lock into said flexible portion.

4. A catheter according to claim 3 wherein said lock is tapered whereby the further the lock is threaded into the flexible portion the greater the expansion of the latter.

5. A catheter according to claim 1 or claim 2 wherein said controlling means includes means for collapsing said flexible portion during insertion of the tube, said flexible portion expanding upon release of said collapsing means thereby to engage the fossa navicularus.

6. A catheter according to claim 2 wherein said tube has a guard member secured to the end thereof adjacent the fossa navicularus, said guard engaging the head of the glans to position the tube properly for subsequent engagement of the securing means.

7. A catheter according to claim 6 wherein said guard member is hollow and includes means for communicating said tube with said external collecting means.

8. A catheter according to claim 3 wherein said locking member is hollow and includes means for communicating said tube with said external collecting means.

* * * * *